United States Patent [19]

Lattrell et al.

[11] 4,148,895

[45] Apr. 10, 1979

[54] BASICALLY SUBSTITUTED INDOLE DERIVATIVES

[75] Inventors: Rudolf Lattrell, Konigstein; Wilhelm Bartmann, Neuenhain; Joachim Kaiser, Camberg, all of Fed. Rep. of Germany

[73] Assignee: Hoechst Aktiengesellschaft, Frankfurt, Fed. Rep. of Germany

[21] Appl. No.: 751,084

[22] Filed: Dec. 16, 1976

[30] Foreign Application Priority Data

Dec. 19, 1975 [DE] Fed. Rep. of Germany ....... 2557341

[51] Int. Cl.² ................. A61K 31/535; C07D 401/14
[52] U.S. Cl. ............................. 424/248.54; 260/243.3; 260/244.4; 260/326.14 R; 424/250; 424/267; 544/121; 544/130; 544/143; 544/144; 544/357; 544/364; 544/373; 546/187; 546/201; 424/248.57; 424/248.58

[58] Field of Search ................. 260/326.14 R, 268 BC; 424/248, 250, 267; 544/121, 130, 143, 357, 364, 373

[56] References Cited

U.S. PATENT DOCUMENTS

| 3,320,278 | 5/1967 | Ruyle et al. ................... 260/268 BC |
| 3,847,920 | 11/1974 | Klutchko et al. ........... 260/326.14 R |
| 3,980,668 | 9/1976 | Buchanan et al. ................... 424/274 |

*Primary Examiner*—Paul M. Coughlan, Jr.
*Attorney, Agent, or Firm*—Curtis, Morris & Safford

[57] ABSTRACT

The present invention relates to basically substituted indole derivatives and to a process for their manufacture.

The novel compounds are valuable medicaments which exhibit hypotensive and antiarrhythmic activity on the cardiac circulation system.

8 Claims, No Drawings

BASICALLY SUBSTITUTED INDOLE DERIVATIVES

The present invention relates to new basically substituted indole derivatives and the physiologically acceptable acid addition salts thereof, to a process for the manufacture of these compounds as well as to pharmaceutical compositions thereof.

It has been found that indole derivatives which carry basic substituents in 2- and/or 3-positions have valuable pharmacological properties, especially on the heart's circulatory system.

Hence, object of this invention are indole derivatives of the formula I

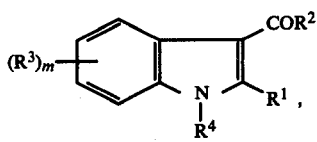

in which:

$R^1$ stands for an amino group of the formula

wherein $R^5$ and $R^6$ are identical or different, and each stands for an alkyl group of 1 to 6 carbon atoms or these alkyl groups together with the nitrogen atom may also form a 5- to 8-membered ring which may carry, at a carbon atom, an alkyl group of 1 to 4 carbon atoms, an alkoxy group of 1 to 4 carbon atoms, a hydroxy, carboxy or alkoxy-carbonyl group of 1 to 4 carbon atoms and in which one of the carbon atoms may be replaced by an oxygen, sulfur or nitrogen atom and the hydrogen atom of the latter may be substituted by the thienyl, furyl, pyridyl, dihydro-pyridyl or formyl group, an alkenyloxycarbonyl group of 3 to 6 carbon atoms or an alkinyloxycarbonyl group of 3 to 6 carbon atoms, an alkoxycarbonyl group of 1 to 4 carbon atoms, which may be substituted by hydroxy or alkoxy of 1 to 4 carbon atoms, the phenyl group which may carry one or more alkyl groups of 1 to 4 carbon atoms, alkoxy groups of 1 to 4 carbon atoms, methylene dioxy, hydroxy, nitro or amino groups or halogen atoms, and the hydrogen atom at the nitrogen atom may further be substituted by the radical —COR$^9$, wherein R$^9$ stands for hydrogen or a phenyl group, optionally having the substituents as mentioned above, or by an alkyl group of 1 to 4 carbon atoms which may be substituted by hydroxy, alkoxy of 1 to 4 carbon atoms, dialkylamino of 1 to 4 carbon atoms, ethylene-dioxy, trimethylene-dioxy or phenyl which may be substituted as mentioned above or by an aminocarbonyl group of the formula

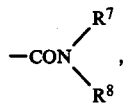

wherein $R^7$ and $R^8$ have the same meanings as $R^5$ and $R^6$, with the proviso that together with the nitrogen atom they may form an unsubstituted heterocyclic ring containing only one hetero atom, $R^2$ stands for a hydrogen atom, a saturated or unsaturated, straight-chained or branched aliphatic hydrocarbon radical of 1 to 6 carbon atoms, a phenyl group which may carry one or more alkyl groups of 1 to 4 carbon atoms, alkoxy groups of 1 to 4 carbon atoms, methylene-dioxy, hydroxy, nitro or amino groups or halogen atoms, or $R^2$ stands for an amino group of the formula

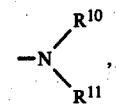

wherein $R^{10}$ and $R^{11}$ have the meanings of $R^5$ and $R^6$ mentioned for $R^1$, or wherein $R^{10}$ stands for hydrogen and $R^{11}$ for an aminoalkyl group of the formula

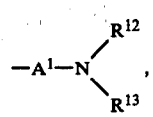

wherein $A^1$ is a single bond or stands for a straight-chained or branched alkylene group of up to 6 carbon atoms which may be substituted by hydroxy groups, alkoxy groups of 1 to 4 carbon atoms or acyloxy groups and wherein $R^{12}$ and $R^{13}$ are identical or different and each stands for hydrogen, cycloalkyl of 5 to 7 carbon atoms, an alkyl group of 1 to 6 carbon atoms which may be substituted by acetoxy, alkoxy of 1 to 4 carbon atoms, acetylamino or formamino, or a phenyl group which may be substituted as mentioned above, or wherein $R^{12}$ and $R^{13}$ together with the nitrogen atom form a 5-, 6- or 7-membered ring which may be substituted, at one carbon atom, by alkyl of 1 to 4 carbon atoms, alkoxy of 1 to 4 carbon atoms, phenyl, hydroxy, carboxy or alkoxycarbonyl of 1 to 4 carbon atoms, and wherein one of the cyclic carbon atoms may be replaced by an oxygen, sulfur or another nitrogen atom and the hydrogen atom at this latter may be substituted as defined for the amino group of the formula

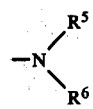

in substituent $R^1$, or $R^{10}$ may stand for hydrogen and $R^{11}$ for alkyl of 1 to 6 carbon atoms which may be substituted by hydroxy, alkoxy of 1 to 4 carbon atoms, alkenyloxy of 3 to 5 carbon atoms, carboxy, alkoxycarbonyl of 1 to 6 carbon atoms, dialkylamino of 1 to 4 carbon atoms, cycloalkyl of 5 to 7 carbon atoms, cycloalkenyl of 5 to 7 carbon atoms, chloro, bromo, pyridyl or phenyl which may be substituted as mentioned above, or $R^{11}$ may stand for cycloalkyl of 5 to 7 carbon atoms which may be substituted by alkyl of 1 to 4 carbon atoms, alkenyl of 2 to 4 carbon atoms, alkinyl of 2 to 4 carbon atoms or dialkylamino of 1 to 4 carbon atoms, or for the 1-adamantyl, norbornyl group or an alkenyl or alkinyl group of each 3 to 10 carbon atoms, or $R^2$ stands for an aminoalkyl group of the formula

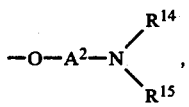

wherein $A^2$ stands for a straight-chained or branched alkylene group of 2 to 6 carbon atoms which may be substituted by alkyl of 1 to 4 carbon atoms or phenyl which may be substituted as mentioned above, and wherein $R^{14}$ and $R^{15}$ have the same meanings as mentioned for $R^{12}$ and $R^{13}$; for a basic radical of the formula $-O-(CH_2)_n-R^{16}$, wherein $R^{16}$ stands for a 5- or 6-membered heterocyclic ring containing a nitrogen atom, and n stands for zero or 1, $R^3$ stands for a hydrogen atom, an alkoxy group of 1 to 5 carbon atoms, the hydroxy group, a chlorine, bromine or fluorine atom, a nitro, amino or benzyloxy group, m stands for an integer of 1, 2 or 3 and $R^4$ stands for a hydrogen atom, a saturated or unsaturated straight-chained or branched, aliphatic hydrocarbon radical of 1 to 6 carbon atoms, a benzyl or phenyl group, in which the phenyl groups may be substituted as mentioned above, as well as the physiologically acceptable salts thereof.

As preferred substituents, there may be mentioned: for $R^1$: the amino group of the formula

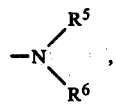

wherein the alkyl groups $R^5$ and $R^6$ together with the nitrogen atom form a 5- to 8-membered ring and one of the carbon atoms may be replaced by a nitrogen or oxygen atom, especially the pyrrolidino, piperidino, hexamethylene-imino, morpholino, 4-hydroxypiperidino, 4-carbethoxy-piperidino and 1-piperazinyl group of the formula

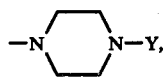

wherein Y stands for hydrogen, alkyl of 1 to 3 carbon atoms, phenylalkyl, wherein the alkyl-group has 1 to 3 carbon atoms, β-hydroxyethyl, 2-(1,3-dioxolan-2-yl)-ethyl, 2-(1,3-dioxan-2-yl)-ethyl, 3,4-methylene-dioxybenzyl, pyrrolidinocarbonylmethyl, phenyl or phenyl substituted by methoxy, chloro or hydroxy; allyl, 2-methallyl, propargyl, 3,4,5-trimethoxybenzoyl, 3,4-methylene-dioxybenzoyl, 2-furoyl, 2-thenoyl, alkoxycarbonyl of up to 5 carbon atoms, wherein the alkyl group of this latter may be substituted by a hydroxy group;

for $R^2$: hydrogen, an amino group of the formula

wherein $R^{10}$ and $R^{11}$ stand for identical alkyl groups of 1 to 4 carbon atoms, or together with the nitrogen atom they form a 5- to 8-membered ring which may be substituted, especially the pyrrolidino, piperidino, hexamethylene-imino, 4-hydroxy-piperidino group, and wherein one of the carbon atoms may be replaced by an oxygen or nitrogen atom, especially the morpholino and 1-piperazinyl groups of the formula

wherein Y stands for alkyl of 1 to 3 carbon atoms, phenylalkyl, wherein the alkyl group has 1 to 3 carbon atoms, β-hydroxyethyl, 2-(1,3-dioxolan-2-yl)-ethyl, 2-(1,3-dioxan-2-yl)-ethyl, 3,4-methylene-dioxy-benzyl, pyrrolidinocarbonylmethyl, phenyl, phenyl substituted by methoxy, chloro, nitro or amino; allyl, propargyl, 3,4,5-trimethoxy-benzoyl, 3,4-methylenedioxy-benzoyl, 2-furoyl, 2-thenoyl, alkoxycarbonyl of 1 to 5 carbon atoms, in which the alkyl group of the latter may be substituted by the hydroxy group, or wherein $R^{10}$ is hydrogen, and $R^{11}$ a cyclohexyl group which is substituted by a dialkylamino group wherein each alkyl has 1 to 3 carbon atoms, or $R^2$ is a group of the formula

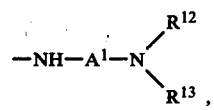

wherein $A^1$ stands for a straight-chained or branched alkylene group of 2 or 3 carbon atoms, which may be substituted by a hydroxy group, and $R^{12}$ and $R^{13}$ stand for straight-chained or branched alkyl groups of 1 to 3 carbon atoms, or $R^{12}$ and $R^{13}$ together with the nitrogen atom form a 5- or 6-membered ring which may contain a hetero atom, especially the piperidino, pyrrolidino, morpholino, 4-methyl-piperazino group;

furthermore, $R^2$ stands for an aminoalkyl group of the formula

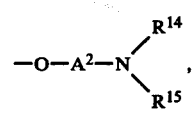

wherein $A^2$ stands for a straight-chained alkylene group of 2 or 3 carbon atoms, and $R^{14}$ and $R^{15}$ are different, $R^{14}$ standing for hydrogen and $R^{15}$ for a straight-chained or branched alkyl group of 1 to 4 carbon atoms or a cyclohexyl group, or $R^{14}$ and $R^{15}$ are identical and stand for alkyl group of 1 to 4 carbon atoms, or together with the nitrogen atom they form a 5- or 6-membered ring which may contain a hetero atom, especially the morpholino, 4-methylpiperazino, piperidino and pyrrolidino groups;

for $R^3$: hydrogen, alkoxy groups of 1 to 4 carbon atoms, especially the methoxy group, preferably in 4-, 5- and/or 6-positions;

for $R^4$: hydrogen, the methyl, phenyl, benzyl group, or a o-, m- or p-alkoxyphenylgroup, wherein the alkoxy group has 1 to 4 carbon atoms, especially the methoxyphenylgroup.

Further object of this invention is a process for the manufacture of the compounds of formula I, which comprises (a) reacting a compound of the formula II

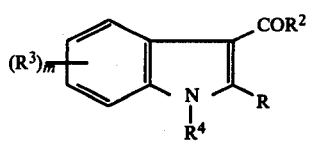   II in which R stands for a chlorine or bromine atom, $R^2$ stands for a hydrogen atom, an alkyl or phenyl group, and $R^3$, $R^4$ and m are defined as in formula I, with an amine of the formula

wherein $R^5$ and $R^6$ are defined as in formula I, or (b) reacting an indole 3-carboxylic acid of the formula III

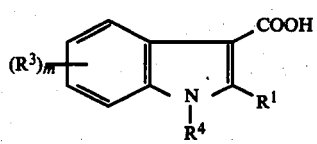   III in which $R^1$, $R^3$, $R^4$ and m are defined as above, with an amine of the formula

or with an alcohol of the formula

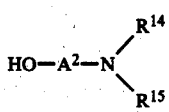

or HO—$(CH_2)_n$—$R^{16}$, wherein $A^2$, $R^{10}$, $R^{11}$, $R^{14}$, $R^{15}$ and $R^{16}$ are defined as in formula I and n is an integer of 0 or 1, or (c) reacting a compound of the formula IV

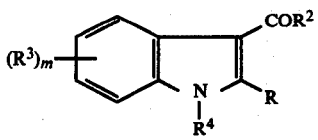   IV in which R stands for a chlorine or bromine atom, $R^3$, $R^4$ and m are defined as in formula I, and $R^2$ stands for an amino group of the formula

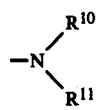

or an aminoalkyloxy group of the formula

or a hydroxy group of the formula HO-$(CH_2)_n$-R, in which $A^2$, $R^{10}$, $R^{11}$, $R^{14}$, $R^{15}$, $R^{16}$ and n are defined as in formula I, with an amine of the formula

wherein $R^5$ and $R^6$ are defined as in formula I, or (d) reacting a compound of the formula V

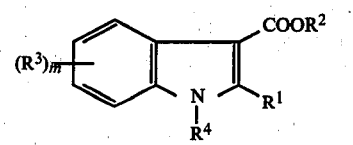   V in which $R^1$ to $R^4$ and m are defined as in formula I, with the proviso that one or the two radicals $R^1$ and $R^2$ contain a secondary amino group, with an alkylating agent of the formula $XR^{17}$, in which X stands for a chlorine or bromine atom and $R^{17}$ for a straight-chained or branched alkyl group of 1 to 6 carbon atoms, which may be substituted by hydroxy, alkoxy of 1 to 4 carbon atoms, dialkylamino of 1 to 4 carbon atoms, ethylene-dioxy, trimethylene-dioxy, or the group

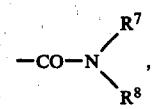

wherein $R^7$ and $R^8$ are defined as in formula I, or by an optionally substituted phenyl group, or for alkenyl or alkinyl of 3 to 8 carbon atoms each, or with a chloroformiate of the formula ClCOO—$(C_1-C_4)$—alkyl, in which the alkyl groups carry hydroxy or alkoxy groups of 1 to 4 carbon atoms, or of the formula ClCOO—$(C_3-C_6)$—alkenyl, or with a compound of the formula $ClCOR^9$, wherein $R^9$ is defined as in formula I, or (e) converting a compound of the formula VI

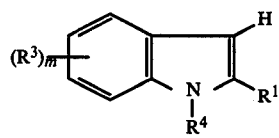   VI in which $R^1$, $R^3$, $R^4$ and m are defined as in formula I, into a compound of formula I either by reaction with phosphorus oxychloride/N,N'-dimethylformamide, if $R^2$ in formula I is hydrogen, or by reaction with an aliphatic or aromatic acid chloride, if $R^2$ in formula I is alkyl or phenyl, or by reaction with a chloroformic acid methyl or ethyl ester, if $R^2$ in formula I is methoxy or ethoxy, or (f) reacting a compound of the formula VII

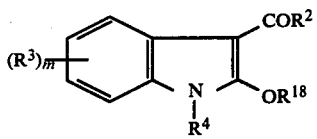

VII in which $R^2$, $R^3$, $R^4$ and m are defined as in formula I, and $R^{18}$ stands for an alkyl group of 1 to 4 carbon atoms or the phenyl group, with an amine of the formula

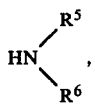

wherein $R^5$ and $R^6$ are defined as above.

According to method step (a), at least twice the equivalent amount of amine is added, since one mol of amine is required to bind the hydrogen halide that has been split off; but in some cases, it is advantageous to use an up to 15-fold excess of amine to accelerate the reaction. As solvents, there are mentioned, inasfar as they are used for the reaction, inert anhydrous organic solvents, such as dioxan, 1,2-dimethoxy-ethane, diethylene-glycol dimethyl ether, diethylene-glycol dibutyl ether, benzene, toluene, xylene, chlorobenzene, dichlorobenzene, trichlorobenzene, N,N'-dimethylformamide, dimethylsulfoxide or hexamethyl-phosphoric acid triamide. The reaction is generally carried out at temperatures of from 50° to 220° C., preferably from 80° to 180° C.

According to method step (b), the carboxylic acids of formula III are converted according to the usual method of ester or amide formation, for example via the acid chlorides or the mixed anhydrides, into the esters or amides. For the esterification with alcohols which still contain secondary amino groups, the salts of the amino alcohols are used.

For the method step (c), the test conditions disclosed for method (a) are applicable.

According to method step (d), the secondary amino groups are reacted according to known methods; for example, formylation is performed by heating with formiates, acylation by reaction with acid chlorides and alkylation with haloalkyl compounds.

According to method step (e), the compounds of formula VI are reacted according to known methods (e.g. A. Deberly and J. Bourdais, Tetrahedron Letters 1971, p. 3049) with acid chlorides, chloroformiates or with dimethylformamide/phosphorus oxychloride.

According to method step (f), the principle of method (a) is followed but, in most cases, higher temperatures are required for the exchange of the alkoxy group as compared to the halogen atom.

The starting compounds for methods (a) to (e) may be prepared as disclosed in copending patent application Ser. No. 751,090 filed Dec. 16, 1976, now abandoned.

According to this patent application, for example, an optionally substituted oxindole is reacted with phosphoroxychloride or -bromide and dimethylformamide in a solvent, for example, toluene, at a temperature of about 30° C. to give the corresponding 2-chloro-(or-bromo)-indol-3-carboxaldehyde. The aldehyde so obtained is then oxidized according to the usual methods, for example potassium permanganate, to give the corresponding carboxylic acid, which can then be converted, according to the usual methods of the ester or amide formation, for example, via an acid chloride or a mixed anhydride, into an ester or an amide. The esterification with alcohols, which additionally contain secondary amino groups, is carried out using the salts of the amino alcohols. The compounds obtained according to the last-mentioned method, can be further alkylated with the usual alkylation agents on the secondary amino group.

The compounds of the invention have valuable therapeutic properties. For example, in addition to other pharmacological properties, they have an effect on the cardiac circulation that appears in a hypotensive effect and especially in an antiarrhythmic activity. Therefore, these compounds are suitable for the treatment of disturbances in the cardiac rhythm. This antiarrhythmic activity was established on dogs that had been poisoned with strophanthin, on cats that had been exposed to hypothermia and by means of the digitoxin-aconitin fibrillation test on the guinea pig-Langendorff heart.

The novel compounds may be used alone or in admixture with pharmacologically acceptable carrier material. For oral administration the active compounds are mixed with the usual substances and brought into the usual dosage unit forms by known methods, for example tablets, gelatin capsules, aqueous, alcoholic or oily suspensions or aqueous, alcoholic or oily solutions. As inert carrier material, there may be used, for example, magnesium carbonate, lactose or corn starch, in conjunction with other substances, for example magnesium stearate. The composition may be in the form of dry or moist granules. Vegetable and animal oils, for example sunflower oil or castor oil are especially useful as oily carrier materials or solvents.

Especially advantageous is the intravenous administration. For this purpose, the active compounds or the physiologically acceptable salts thereof are dissolved together with the usual substances. Such physiologically acceptable salts are formed with the following acids, for example: hydrochloric acid, hydrobromic acid or hydroiodic acid, phosphoric acid, sulfuric acid, methyl-sulfuric acid, amidosulfonic acid, nitric acid; formic acid, acetic acid, propionic acid, succinic acid, tartaric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-aminosalicyclic acid, hydroxyethane-sulfonic acid, benzene-sulfonic acid, or synthetic resins containing acid groups, for example those having an ion exchanger effect.

As solvents of the corresponding physiologically acceptable salts of the active compounds suitable for intravenous administration, there are mentioned, for example, water, a physiological sodium chloride solution or alcohols, for example ethanol, propane-diol or glycerol; furthermore, sugar solutions, for example glucose or mannitol solutions, or mixtures of the various solvents mentioned.

For oral administration, the single dose is within the range of from 50–1,000 mg, preferably from 100–500 mg, for the intravenous or intramuscular administration, it is within the range of from 20–100 mg, preferably 50 mg.

The daily dose in each case is for the oral administration within the range of from 50–2,000 mg, preferably 500 mg, for the intravenous or intramuscular administration within the range of from 20–500 mg, preferably 100 mg. The pharmacological effect has been tested on rats.

The following Examples illustrate the invention.

EXAMPLE 1

1-Phenyl-2-piperazino-3-indole carbaldehyde

A mixture of 51.2 g (0.2 mol) of 2-chloro-1-phenyl-3-indole carbaldehyde and 172 g (2 mols) of anhydrous piperazine in 500 ml of dioxan free of peroxides was refluxed for 22 hours. After cooling, the mixture was diluted with 1.5 l of water, the crystal mass that had separated was suction-filtered after standing overnight and washed with water. After drying, the product was recrystallized from ethyl acetate.

Yield: 46 g (75% of the theoretical yield) of yellowish crystals which melted at 176–178° C.; the hydrochloride melted at 260° C.

The 2-substituted indole 3-aldehyde derivatives of the Examples listed in Table 1 were prepared as above from 2-chloro-indole 3-carbaldehyde and the corresponding bases.

EXAMPLE 7

1-Phenyl-2-(1-piperazinyl)-indole 3-carboxylic acid (4-methyl)-Piperazide 106 g (0.3 mol) of 2-chloro-1-phenyl-indole 3-carboxylic acid (4-methyl)-piperazide and 258 g (3 mols) of piperazine were refluxed for 17 hours in 1 l of diethylene-glycol dimethyl ether. After cooling, the mixture was diluted with water, extracted twice with methylene chloride and the solvent was eliminated in vacuo. The oily residue was dissolved in 300 ml of ethyl acetate while heating and allowed to stand overnight at +5° C. The precipitate was suction-filtered and washed with ethyl acetate.

Yield: 111 g (91 % of the theoretical yield) of light-brown crystals, m.p. 201–202° C.; dihydrochloride decomposed above 280° C.

The substituted 1-phenyl-indole 3-carboxylic acid derivatives of formula I as listed in the Examples of Table 2 and the pharmacologically useful salts thereof were prepared according to Example 7 from the 2-chloro-1-phenyl-indole 3-carboxylic acid derivatives ($R^1$ = Cl) and the corresponding bases.

TABLE 1

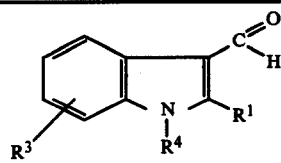

| Example | $R^1$ | $R^3$ | $R^4$ | m.p. ° C, salt (m.p. ° C.) |
|---|---|---|---|---|
| 2 | —N⟨NCH₃⟩ (piperazinyl-NCH₃) | H | $C_6H_5$ | 180°; hydrochloride (240 – 242°) |
| 3 | —N⟨N—CH₂CH₂OH⟩ | H | $C_6H_5$ | resin; hydrochloride (214 – 216°) |
| 4 | —N⟨NC₆H₅⟩ | H | $C_6H_5$ | 167 – 168° |
| 5 | —N⟨NCH₃⟩ | H | m-CH₃O—C₆H₄ | amorphous; hydrochloride (230 – 232°) |
| 6 | —N⟨NCH₃⟩ | 5-CH₃O | CH₃ | amorphous; hydrochloride (decomp. >250°) |

TABLE 2

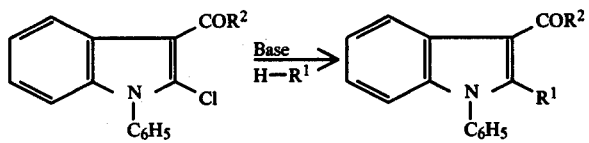

| Example | $R^2$ | $R^1$ | melt.p. ° C, salt (m.p. ° C.) |
|---|---|---|---|
| 8 | 4-methyl-1-piperazinyl | 4-methyl-1-piperazinyl | 150°; Di-HCl (220°) |
| 9 | 4-methyl-1-piperazinyl | morpholino | 196–197°; HCl (255°) |
| 10 | 4-methyl-1-piperazinyl | piperidino | 165–166°; HCl (240°) |
| 11 | dimethylamino | 4-methyl-1-piperazinyl | 178°; HCl (230°) |
| 12 | dimethylamino | 1-piperazinyl | 211°; HCl (230°) |
| 13 | dimethylamino | 4-phenyl-1-piperazinyl | 166° |
| 14 | 1-piperazinyl | 1-piperazinyl | 160–163°; Di-HCl (270°) |
| 15 | 1-piperazinyl | morpholino | 120–123°; HCl (270–272°) |
| 16 | 1-piperazinyl | piperidino | 152°; HCl (215°) |
| 17 | 4-phenyl-1-piperazinyl | 1-piperazinyl | 176–178°; HCl (210°) |
| 18 | 4-phenyl-1-piperazinyl | 4-methyl-1-piperazinyl | 179°; HCl (200°) |
| 19 | 4-phenyl-1-piperazinyl | piperidino | 206°; HCl (190°) |

TABLE 2-continued

Reaction scheme:

Starting material: indole with COR² at 3-position, Cl at 2-position, N-C₆H₅

$$\text{(2-Cl-indole-COR}^2\text{)} \xrightarrow[\text{H—R}^1]{\text{Base}} \text{(2-R}^1\text{-indole-COR}^2\text{)}$$

| Example | R² | R¹ | melt.p. ° C., salt (m.p. ° C.) |
|---|---|---|---|
| 20 | 4-phenyl-1-piperazinyl | morpholino | 201–203°; HCl (190°) |
| 21 | 4-hydroxyethyl-1-piperazinyl | 1-piperazinyl | 144–146°; Di-HCl (240°) |
| 22 | 4-hydroxyethyl-1-piperazinyl | 4-methyl-1-piperazinyl | 130–131°; Di-HCl (210°) |
| 23 | 4-hydroxyethyl-1-piperazinyl | morpholino | 134–135°; HCl (220°) |
| 24 | piperidino | 1-piperazinyl | 190°; HCl (290–291°) |
| 25 | piperidino | 4-methyl-1-piperazinyl | 151°; HCl (278°) |
| 26 | morpholino | 1-piperazinyl | Harz; HCl (246°) |
| 27 | morpholino | 4-methyl-1-piperazinyl | 169–170°; HCl (280°) |
| 28 | pyrrolidino | 1-piperazinyl | Harz; HCl (Zers. >300°) |
| 29 | pyrrolidino | 4-methyl-1-piperazinyl | Harz; HCl (265°) |
| 30 | —NHCH₂CH₂N(morpholino) | 1-piperazinyl | 172–173°; Di-HCl (250°) |
| 31 | —NHCH₂CH₂N(morpholino) | 4-methyl-1-piperazinyl | 156–157°; Di-HCl (190°) |
| 32 | —NHCH₂CH(OH)CH₂N(C₂H₅)₂ | 1-piperazinyl | 129°; Di-HCl (210°) |
| 33 | —NH—(cyclohexyl with C≡CH) | 1-piperazinyl | 187°; HCl (190–193°) |
| 34 | —NH—(cyclohexyl with C≡CH) | 4-methyl-1-piperazinyl | 192°; HCl (176–178°) |
| 35 | 4-Methyl-1-piperazinyl | 3-methyl-1-piperazinyl | 107°; Di-HCl (decomp. >310°) |
| 36 | —NH—N(NCH₃ piperazine) | 1-piperazinyl | 56–58°; Di-HCl; >280° |
| 37 | —NH—(cyclohexyl)—N(C₂H₅)₂ | morpholino | amorphous; hydrochloride, decomp. >230° |
| 38 | —NH—(cyclohexyl)—N(C₂H₅)₂ | 1-piperazinyl | 194°; Di-HCl; decomp. >260° |
| 39 | —NH—(cyclohexyl)—N(C₂H₅)₂ | 4-methyl-1-piperazinyl | 192°; Di-HCl; decomp. 270° |

EXAMPLE 40

2-(4-Methyl-1-piperazinyl)-1phenyl-indole 3-carboxylic acid (4-hydroxy) piperidine To a solution that had been cooled to −20° C. and which consisted of 14.5 g (0.05 mol) of 2-chloro-1-phenyl-indole 3carboxylic acid chloride in 30 ml of chloroform, a mixture of 6 g (0.06 mol) of 4-hydroxy-piperidine, 8 ml of pyridine and 10 ml of chloroform was added. The mixture was allowed to stand for 2 hours at room temperature and then washed with dilute hydrochloric acid and with water. The resinous residue of the organic phase was chromatographed using silica gel 60 (0.06–0.2 mm, deactivated by 10% of water, column size: 4 × 110 cm) with chloroform containing 5% methanol. After elution of 1.3 l, the 2-chloro-1-phenyl-indole 3-carboxylic acid (4-hydroxy)-piperidine was eluted as a resin. The yield was 12 g (68% of the theoretical yield). A mixture of 5.3 g (15 mmols) of this resin, 15 g of N-metyhl-piperazine and 50 ml of diglym was heated to the boil for 24 hours, the cooled mixture was then worked up as in Example 7. The crystallized residue of the organic phase was digested with ether to yield 5 g (80%) of the product, m.p. 195° C.; the hydrochloride melted at 160–165° C.

EXAMPLE 41

The following substituted 1-phenyl-indole 3-carboxylic acid derivatives of formula I listed in Table 3 were prepared according to Example 7 and Example 40 from 2-chloro-1phenyl-indole 3-carboxylic acid derivatives of formula I (R¹ = Cl) and the corresponding amines.

TABLE 3

Structure: indole with COR² at 3-position, R¹ at 2-position, C₆H₅ at N.

| R² | R¹ |
|---|---|
| 3-hydroxymethylpiperidino | 1-piperazinyl |
| 4-hydroxy-piperidino | 1-piperazinyl |
| 4-ethoxycarbonyl-piperidino | 1-piperazinyl |
| 3-methyl-piperidino | 1-piperazinyl |
| 3,5-dimethylmorpholino | 1-piperazinyl |
| 4-phenylpiperidino | 1-piperazinyl |
| hexamethylenimino | 1-piperazinyl |
| heptamethylenimino | 1-piperazinyl |
| —NHCH₂CH₂OCH₃ | 4-methyl-1-piperazinyl |
| —N(CH₃)CH₂CH₂OH | 4-methyl-1-piperazinyl |
| —NHCH₂CH(OH)CH₂Cl | 4-methyl-1-piperazinyl |
| —NH(CH₂)₃COOH | 4-methyl-1-piperazinyl |
| —NHCH₂CH₂NHCOCH₃ | 4-methyl-1-piperazinyl |
| —NHCH₂CH(OH)CH₂OCH₂CH=CH₂ | 4-methyl-1-piperazinyl |
| | 4-methyl-1-piperazinyl |
| —NHC(C₂H₅)₂C≡CH | 4-methyl-1-piperazinyl |
| —NHC(CH₃)₂CH₂CH₃ | 4-methyl-1-piperazinyl |
| | 4-methyl-1-piperazinyl |
| —NH—⟨cyclohexyl-CH₃⟩ | |
| —NHCH₂CH₂CH(C₆H₅)₂ | 4-methyl-1-piperazinyl |
| —NHCH₂CH₂CH(C₆H₅)—(pyridyl) | 4-methyl-1-piperazinyl |
| —NHCH₂CH₂N(C₂H₅)₂ | 4-hydroxy-piperidino |
| —NHCH₂CH₂N(C₆H₅)₂ | 4-ethoxycarbonyl-piperidino |
| | morpholino |
| —NH(CH₂)₃NH—⟨cyclohexyl⟩ | |
| | morpholino |
| —HNCH₂N⟨piperidino⟩ | |
| | morpholino |
| —HN(CH₂)₃N⟨piperazinyl⟩N—CH₂CH₂OH | |
| | 1-piperazinyl |
| —N⟨piperazinyl⟩N—(O—CH₃O)C₆H₄ | |
| | 1-piperazinyl |
| —N⟨piperazinyl⟩N—(p-NH₂)C₆H₄ | |
| | 1-piperazinyl |
| —HN—N⟨azepanyl⟩ | |
| | 4-methyl-1-piperazinyl |
| —HN—N⟨azepanyl⟩ | |
| | 4-methyl-1-piperazinyl |
| —HN—N⟨morpholino⟩O | |

TABLE 3-continued

| R² | R¹ |
|---|---|
| —HN—N⟨2,6-dimethylpiperidino⟩ (CH₃ at 2 and 6) | 4-methyl-1-piperazinyl |

EXAMPLE 42

1-(3-Methoxy phenyl)-2-(1-piperazinyl)-indole 3-carboxylic acid (4-methyl)-piperazide To a solution of 3.2 g (10 mmols) of 2-chloro-1-(3-methoxyphenyl)-indole 3-carboxylic acid chloride in 20 ml of chloroform, a mixture pf 2.2 ml of N-methyl-piperazine, 2.4 ml of pyridine and 5 ml of chloroform was added while cooling. After standing for 1 hour at room temperature, the mixture was washed twice with water, and the solvent was evaporated in vacuo. The resinous residue, which was uniform according to thin-layer chromatography and consisted of 2-chloro-1-(3-methoxyphenyl)-indole 3-carboxylic acid (4-methyl)-piperazide, was dissolved in 40 ml of diglym, and after addition of 13 g (0.15 mol) of piperazine, the solution was heated to the boil. The cooled solution was diluted with methylene chloride, washed three times with water, and the solvent was eliminated in vacuo. The resinous residue was dissolved in chloroform, and an excess of ethanolic hydrochloric acid was added. The solvent was eliminated in vacuo, the crystallized residue was digested with acetone, suction-filtered and washed with acetone. The yield of faintly grey-colored dihydrochloride of the above compound amounted to 3.7 g (73% of the theoretical yield), m.p. 228–230° C.

EXAMPLE 43

1-(3-Methoxyphenyl)-2-(4-methyl-1-piperazinyl)-indole 3-carboxylic acid morpholide This compound was prepared from 2-chloro-1(3-methoxyphenyl)-indole-3-carboxylic acid chloride and morpholine to yield 2-chloro-1-(3-methoxyphenyl)-indole 3-carboxylic acid morpholide which was reacted with N-methyl-piperazine according to Example 42. The yield of amorphous product was 85% of the theoretical yield; the amorpheus hydrochloride had a decomposition point above 160° C.

EXAMPLE 44

Starting from 2-chloro-1-(3-methoxyphenyl)-indole 3-carboxylic acid chloride, the substituted 1-(3-methoxyphenyl)-indole 3-carboxylic acid derivatives of formula I and the pharmacologically useful salts thereof were prepared via the 2-chloro-1-(3-methoxyphenyl)-indole 3-carboxylic acid derivatives of formula I by reaction with the corresponding bases according to Examples 42, 40 and 7. The radicals $R^1$ and $R^2$ are listed in Tables 2 and 3

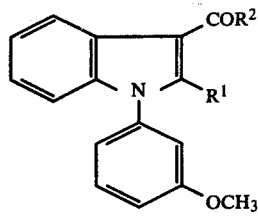

EXAMPLE 45

5-Methoxy-1-methyl-2-(1-piperazinyl)-indole 3-carboxylic acid (4-methyl)-piperazide In a manner analogous to Example 42, 2-chloro-5-methoxy-1-methyl-indole 3-carboxylic acid chloride was first converted into 4-methyl-piperazide, m.p. 124–125° C., which reacted with piperazine in boiling diglym to yield the above compound, m.p. 151–152° C.; the dihydrochloride had a melting point of 230–232° C. The yield was 87% of the theoretical yield.

EXAMPLE 46

Starting from 2-chloro-5-methoxy-1-methyl-indole 3-carboxylic acid chloride, the substituted 5-methoxy-1-methyl-indole 3-carboxylic acid derivatives of formula I and the pharmacologically useful salts thereof were prepared via 2-chloro-5-methoxy-1-methyl-indole 3-carboxylic acid derivatives of formula I by reaction with the corresponding bases according to Examples 45, 42, 40 and 7. The radicals $R^1$ and $R^2$ are listed in Tables 2 and 3

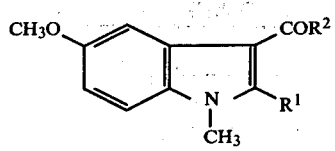

EXAMPLE 47

The following substituted indole 3-carboxylic acid derivatives of formula I listed in Table 4 were prepared according to Examples 7, 40, 42 and 45 from the 2-chloro-indole 3-carboxylic acid chlorides via the 2-chloro-indole 3-carboxylic acid derivatives of formula I by reaction with the amines of formula $HR^1$.

TABLE 4

| $R^1$ | $R^2$ | $R^3$ | $R^4$ |
|---|---|---|---|
| 4-methyl-1-piperazinyl | 1-piperazinyl | 4-Cl | H |
| 4-methyl-1-piperazinyl | 1-piperazinyl | 5-Br | H |
| 4-methyl-1-piperazinyl | 4-hydroxyethyl-1-piperazinyl | 7-Cl | H |
| 1-piperazinyl | 4-hydroxyethyl-1-piperazinyl | 5-$NO_2$ | H |
| 1-piperazinyl | 4-hydroxyethyl-1-piperazinyl | 5-$NH_2$ | H |
| 1-piperazinyl | 4-methyl-1-piperazinyl | 5,7-Di—Br | H |
| 1-piperazinyl | 4-methyl-1-piperazinyl | H | $C_6H_5CH_2$— |
| morpholino | 4-methyl-1-piperazinyl | 5-F | $CH_3$ |
| 4-methyl-1-piperazinyl | 4-methyl-1-piperazinyl | 5-F | $C_2H_5$ |
| 4-methyl-1-piperazinyl | 4-methyl-1-piperazinyl | 5-Cl | n-$C_3H_7$ |
| 4-methyl-1-piperazinyl | 4-methyl-1-piperazinyl | 5-Br | n-$C_4H_9$ |
| 4-methyl-1-piperazinyl | morpholino | 5-$NO_2$ | $CH_3$ |
| 4-methyl-1-piperazinyl | morpholino | 5-$NH_2$ | $CH_3$ |
| 4-methyl-1-piperazinyl | morpholino | 4-$CH_3O$ | $CH_3$ |
| 4-methyl-1-piperazinyl | morpholino | 7-$CH_3O$ | $CH_3$ |
| 4-methyl-1-piperazinyl | piperidino | 5-$C_2H_5O$ | $CH_3$ |
| 4-methyl-1-piperazinyl | piperidino | 5-$C_3H_7O$ | $CH_3$ |
| 1-piperazinyl | piperidino | 5-$C_4H_9O$ | $C_6H_5$ |
| 1-piperazinyl | piperidino | 5-$C_5H_{11}O$ | $CH_3$ |
| 1-piperazinyl | pyrrolidino | 6-$C_2H_5O$ | $C_6H_5$ |
| 1-piperazinyl | pyrrolidino | 6-$C_3H_7O$ | $C_6H_5$ |
| 1-piperazinyl | pyrrolidino | 6-$C_4H_9O$ | $CH_3$ |
| 1-piperazinyl | pyrrolidino | 6-$C_6H_5CH_2O$ | $C_6H_5$ |
| 4-methyl-1-piperazinyl | 4-methyl-1-piperazinyl | 5,6-Di—$CH_3O$ | $CH_3$ |
| 4-methyl-1-piperazinyl | 4-methyl-1-piperazinyl | 5,6-Di—$C_2H_5O$ | $C_6H_5$ |
| piperazinyl | 4-methyl-1-piperazinyl | 5-$C_2H_5O$,6-$CH_3O$ | $CH_3$ |
| piperazinyl | 4-methyl-1-piperazinyl | 5,6-Di—$C_3H_7O$ | $CH_3$ |

EXAMPLE 48

2-(4-Methyl)-1-piperazinyl-1-phenyl-indole 3-carboxylic acid-2-morpholino ethyl ester 11.5 g (0.03 mol) of 2-chloro-1-phenyl-indole 3-carboxylic acid 2-morpholino-ethyl ester (as in Example 8) and 30 g (0.3 mol) of N-methyl-piperazine in 90 ml of diethylene-glycol methyl ether were maintained at 125° C. for 17 hours. After cooling, the mixture was diluted with water, extracted twice with methylene chloride, the organic phase was freed from the solvent in vacuo and the crude resinous base was purified by chromatography using silica gel 60 (0.06–0.2 mm, deactivated by 10% of water, column size: 3 × 130 cm) with chloroform containing 10% methanol. The above compound was eluted as a resin and converted with ethanolic hydrochloric acid into a colorless dihydrochloride having a melting point of 190 to 193° C. The yield was 9 g (67% of the theoretical yield).

The substituted indole 3-carboxylic acid esters of formula I, listed in Table 5, were prepared according to Example 48 from the 2-chloro-1-phenyl-indole 3-carboxylic acid esters and the corresponding base.

TABLE 5

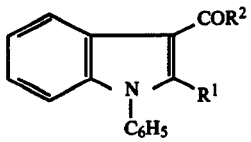

| Example No. | R² | R¹ | m.p. °C, salt (m.p. °C) |
|---|---|---|---|
| 49 | —OCH₂CH₂N⟨morpholino⟩ | -1-piperazinyl | resin, Di—HCl (decomp. 190°) |
| 50 | —OCH₂CH₂NH—⟨C₆H₁₁⟩ | 4-methyl-1-piperazinyl | resin, Di— (255–256°) |
| 51 | —OCH₂CH₂NH—⟨C₆H₁₁⟩ | 1-piperazinyl | resin, Di—HCl (283°) |
| 52 | —OCH₂CH₂NH—⟨C₆H₁₁⟩ | morpholino | 106°, HCl (260°) |

EXAMPLE 53

The following substituted indole 3-carboxylic acid esters of formula I listed in Table 6 were prepared according to Example 48 from 2-chloro-indole 3carboxylic acid esters of formula I and the corresponding bases.

TABLE 6

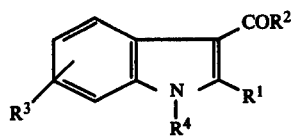

| R¹ | R² | R³ | R⁴ |
|---|---|---|---|
| 1-piperazinyl | —OCH₂CH₂N(C₂H₅)₂ | H | C₆H₅ |
| 1-piperazinyl | —OCH₂CH₂N(CH₃)₂ | 6-CH₃O | C₆H₅ |
| 1-piperazinyl | —O(CH₂)₃N(CH₃)₂ | 5-CH₃O | CH₃ |
| 1-piperazinyl | | 5,6-Di-CH₃O | CH₃ |
| | —OCH₂CH₂N⟨O⟩ | | |
| 1-piperazinyl | —OCH₂CH₂N⟨NH⟩ | 7-CH₃O | CH₃ |
| 1-piperazinyl | —OCH(C₆H₅)CH₂NH—⟨H⟩ | 6-C₃H₇O | C₆H₅ |
| 4-methyl-1-piperazinyl | —OCH₂CH₂NHCH(CH₃)₂ | 6-C₂H₅O | C₆H₅ |
| 4-methyl-1-piperazinyl | —OCH—CH₂NH₂ / CH₂Cl | 6-C₆H₅CH₂O | C₆H₅ |
| 4-methyl-1-piperazinyl | —O—⟨NH⟩ | 5-C₆H₅CH₂O | C₆H₅ |
| 4-methyl-1-piperazinyl | —OCH₂CH₂N⟨C₅H₁₀⟩ | 5-C₃H₇O | CH₃ |
| morpholino | —OCH₂CH₂N⟨pyrrolidine⟩ | 5-C₅H₁₁O | CH₃ |
| morpholino | —O—⟨NCH₃⟩ | H | C₆H₅ |
| piperidino | —OCH₂—⟨N-CH₃ piperidine⟩ | H | C₆H₅ |
| 1-piperazinyl | —O—⟨pyridyl⟩ | H | C₆H₅ |

EXAMPLE 54

2-[4-(2-(1,3-dioxolan-2-yl)-ethyl)-1-piperazinyl]-1-phenyl indole 3-carboxylic acid (4-methyl)-piperazide A stirred mixture of 8 g (0.02 mol) of 1-phenyl-2-(1-piperazinyl)-indole 3-carboxylic acid (4-methyl)-piperazide, 9.45 g (0.07 mol) of 2-(2-chloroethyl)-1,3-dioxolane and 9.7 ml of triethylamine in 60 ml of toluene was maintained at the boil for 40 hours. After cooling, the mixture was diluted with 200 ml of chloroform, washed three times with water, and the solvent was eliminated in vacuo. The resinous residue of the organic phase was chromatographed using silica gel 60 (0.06–0.2 mm, deactivated by 10% of water, column size: 3 × 100 cm)

with chloroform containing 10% methanol. The base was eluted as a resin. The yield amounted to 6.6 g (66% of the theoretical yield). The dihydrochloride melted at 215-217° C.

EXAMPLE 55

2-[4-(3,4-methylene-dioxy-benzyl)-1-piperazinyl]-1-phenyl-indole 3-carboxylic acid 4-methyl-piperazide This compound was prepared from 1-phenyl-2-(1-piperazinyl)-indole 3-carboxylic acid 4-methyl-piperazide and piperonyl chloride in boiling toluene according to Example 54. The resinous base was converted into a colorless dihydrochloride which melted at 210-212° C. The yield was 52% of the theoretical yield.

EXAMPLE 56

The compounds listed in Table 7 were prepared from the 1-piperazinyl compounds of formula I and the corresponding alkyl halides according to Examples 54 and 55.

TABLE 7

| R | $R^2$ | $R^3$ | $R^4$ |
|---|---|---|---|
| —CH$_2$CH$_2$C(OCH$_2$CH$_2$O) | morpholino | H | $C_6H_5$ |
| —CH$_2$C≡CH | 4-phenyl-1-piperazinyl | H | $CH_3$ |
| —CH$_2$C≡CCH$_3$ | piperidino | H | $C_2H_5$ |
| —CH$_2$CH═CH$_2$ | pyrrolidino | H | $C_6H_5$ |
| —CH$_2$CON(hexamethylenimino ring) | hexamethylenimino | 6-CH$_3$O | $C_6H_5$ |
| —CH$_2$CON(morpholino ring) | piperidinoamino | 5-CH$_3$O | $CH_3$ |
| —CH$_2$C$_6$H$_5$ | 4-methyl-1-piperazinyl | 5,6-Di-CH$_3$O | $CH_3$ |
| —CH$_2$CONHCH$_3$ | 4-methyl-1-piperazinyl | 6-C$_2$H$_5$O | $C_6H_5$ |
| —CH$_2$CH$_2$N(C$_2$H$_5$)$_2$ | 4-methyl-1-piperazinyl | H | $C_6H_5$ |

EXAMPLE 57

The compounds of Examples 54, 55 and 56 were alternatively prepared by reaction of 2-chloro-indole 3-carboxylic acid derivatives of formula I with the corresponding alkylated piperazines according to Examples 7, 40, 42 and 45.

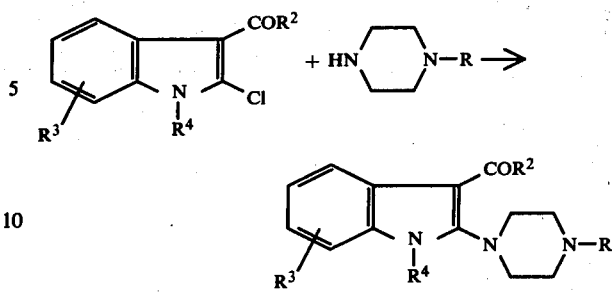

EXAMPLE 58

2-(4-methyl-1-piperazinyl)-1-phenyl-indole 3-carboxylic acid [4-(2-1, 3-dioxolan-2-yl)-ethyl]-piperazide This compound was prepared from 2-(4-methylpiperazinyl)-1-phenyl-indole 3-carboxylic acid piperazide and 2-(2-chloroethyl)-1,3-dioxolane according to Example 54; amorphous; dihydrochloride decomposed above 260° C.

EXAMPLE 59

The compounds listed in Table 8 were prepared from the indole 3-carboxylic acid piperazides and the corresponding alkyl halides according to Example 54.

TABLE 8

| R | $R^1$ | $R^3$ | $R^4$ |
|---|---|---|---|
| —CH$_2$-(3,4-methylenedioxyphenyl) | 4-methyl-1-piperazinyl | H | $C_6H_5$ |
| —CH$_2$CH$_2$C(OCH$_2$CH$_2$O) | morpholino | H | $CH_3$ |
| —CH$_2$C≡CH | piperidino | 6-CH$_3$O | $C_6H_5$ |
| —CH$_2$C═CH$_2$ (H) | 4-(2-hydroxyethyl)-1-piperazinyl | 5-CH$_3$O | $CH_3$ |
| —CH$_2$CON(hexamethylenimino) | hexamethylenimino | 6-C$_2$H$_5$O | $C_6H_5$ |
| —CH$_2$CH$_2$N(C$_2$H$_5$)$_2$ | morpholino | H | $C_6H_5$ |

EXAMPLE 60

2-[4-(2-furoyl)-1-piperazinyl]-1-phenyl-indole 3-carboxylic acid 4-methyl-piperazide To a mixture of 16.1 g (0.04 mol) of 1-phenyl-2-(1-piperazinyl)-indole 3-carboxylic acid 4-methyl piperazide (Example 7), 5 ml of pyridine and 40 ml of chloroform, that had been cooled to −20° C., a solution of 6.5 g (0.05 mol) of furan-2-yl carboxylic acid chloride in 80 ml of chloroform was added. The mixture was allowed to stand for 4 hours at room temperature, then 200 ml of chloroform were added and the mixture was washed four times with water. The solvent was eliminated in vacuo, the crystallized residue was digested with ether, suction-filtered and washed with ether. Yield: 19 g (95% of the theoretical yield), m.p. 180–181° C.; the hydrochloride decomposed above 300° C.

EXAMPLE 61

1-Phenyl-2-[4-(3,4,5-trimethoxy-benzoyl)-1-piperazinyl]-indole 3-carboxylic acid 4-methyl-piperazide This compound was prepared from 2-chloro-1-phenyl-indole 3-carboxylic acid 4-methyl-piperazide and 3,4,5-trimethoxy benzoic acid piperazide in boiling diglym according to Examples 7, 40, 42 and 45. The yield of amorphous product amounted to 77% of the theoretical yield. The hydrochloride melted at 253–255° C.

EXAMPLE 62

2-(4-Ethylcarbonyl-1-piperazinyl)-1-phenyl-indole 3-carboxylic acid 4-methyl-piperazide A mixture of 4 g (10 mmols) of 1-phenyl-2-(1-piperazinyl)-indole 3-carboxylic acid 4-methyl-piperazide, 10 ml of ethyl chloroformiate and 40 ml of ethanol were heated at the boil for 24 hours. After cooling, the precipitate was suctionfiltered and washed with ethanol. The yield amount of 4.2 g in the form of hydrochloride that decomposed above 300° C.

EXAMPLE 63

2-(4-Isobutoxycarbonyl-1-piperazinyl)-1-phenyl-indole 3-carboxylic acid 4-methyl-piperazide This compound was prepared from 2-chloro-1-phenyl-indole 3-carboxylic acid 4-methyl-piperazide and 1-piperazino-carboxylic acid isobutyl ester in boiling diglym according to Example 7 or in ethanol as a solvent in an autoclave at 150° C. After a reaction time of 24 hours, in this case, the solvent was eliminated, the residue was digested with water, and the undissolved product was recrystallized from ethyl acetate/diisopropyl ether. M.p. 132–133° C.; yield: 81% of the theoretical yield. The hydrochloride melted at 314–316° C.

EXAMPLE 64

The compounds listed in Table 9 were prepared according to Examples 60 and 62 from the corresponding 1-piperazinyl compounds of formula I or according to Examples 61 and 63 from the 2-chloro-indole 3carboxylic acid derivatives of formula I and the substituted piperazines.

TABLE 9

| R | $R^2$ | $R^3$ | $R^4$ |
|---|---|---|---|
| −CO−(1,3-benzodioxol-5-yl) | 4-methyl-piperazinyl | 6-$CH_3O$ | $C_6H_5$ |
| −CO−(pyridin-3-yl) | 4-methyl-piperazinyl | 5-$CH_3O$ | $CH_3$ |
| −CO−(pyridin-4-yl) | 4-methyl-piperazinyl | 5-$CH_3O$ | $C_2H_5$ |
| −CO−(1-methyl-1,2,5,6-tetrahydropyridin-3-yl) | morpholino | 5,6-Di$CH_3O$ | $CH_3$ |
| −$COOCH_2$−CH=$CH_2$ | $NHCH_2CH_2N(C_2H_5)_2$ | 6-$C_2H_5O$ | $C_6H_5$ |
| −$COOCH_2$−C($CH_3$)($CH_3$)−CH(O−)(−O−) (cyclic) | 4-methyl-piperazinyl | H | $C_6H_5$ |
| −$COOCH_2C\equiv CH$ | 4-methyl-piperazinyl | H | $C_6H_5$ |
| −COO−$CH_2$−C($CH_3$)=$CH_2$ | 4-methyl-piperazinyl | 6-$C_6H_5CH_2O$ | $C_6H_5$ |

EXAMPLE 65

The substituted indole 3-carboxylic acid piperazides of formula I were prepared according to Examples 60, 61, 62, 63 and 64. Corresponding radicals $R^1$, $R^3$ and $R^4$ are listed in the Tables 8 and 9, the radicals R are given in Examples 60 to 64 and in Table 9.

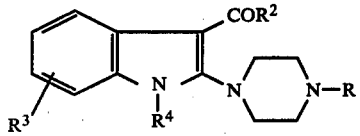

EXAMPLE 66

1-Phenyl-2-(1-piperazinyl)-indole 3-carboxylic acid-[4-(3,4-methylene-dioxybenzyl)]-piperazide 4,74 g (10 mmols) of 2-chloro-1-phenyl-indole 3-carboxylic acid-[4-(3,4-methylenedioxybenzyl)] piperazide and 8.6 g (0.1 mol) of piperazine were heated under reflux during 20 hours in 25 ml of diglyme. The cold solution was worked up as described in Example 42. The crystalline residue of the organic phase was digested with diisopropyl ether, suctionfiltered and washed.

Melting point: 127–129° C., yield: 72% of the theory. The dihydrochloride had a melting point of 241° C. (decomposit.)

EXAMPLE 67

2-[4-(2-Methyl-2-propenyl)oxycarbonyl-1-piperazinyl]-1-phenylindole-3-carboxylic acid-4-methyl-piperazide Reaction in analogy to Example 60 from 1-phenyl-2-(1-piperazinyl)-indole-3-carboxylic acid-4-methyl-piperazide and chloroformic acid-2-methyl-2-propenyl ester. After working up with methylene chloride and heated sodium carbonate solution, the crystalline residue of the organic phase was triturated with ether, suction-filtered and washed with ether. Melting point: 141–143° C., yield: 94% of the theory.

EXAMPLE 68

2-[4-(2-Hydroxy-2-methylpropyl)-oxycarbonyl-1-piperazinyl)]-1-pheny-indole-3-carboxylic acid-4-methyl-piperazide 3 g of 2-[4-(2-methyl-2-propenyl)oxycarbonyl-1-piperazinyl]-1-phenyl-indole-3-carboxylic acid-4-methyl-piperazide were stirred in 30 ml of 50% aqueous sulfuric acid for 20 hours at room temperature. The mixture was worked up with ice, concentrated sodium hydroxide solution and methylene chloride, the crystalline residue of the organic phase was digested with diisopropyl ether.

Yield: 90% of colorless product, melting point: 165–166° C. The hydrochloride had a melting point of about 260° C. (decomposition).

What is claimed is:

1. A compound of the formula

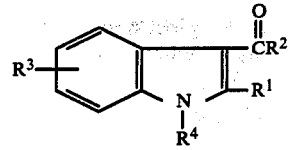

or a physiologically acceptable salt thereof wherein
$R^1$ is piperidino, morpholino, piperazino, or piperazino substituted in the 4-position by
  (a) alkyl having 1 to 3 carbon atoms
  (b) β-hydroxyethyl
  (c) 2-(1,3-dioxolan-2-yl)-ethyl
  (d) phenyl
  (e) 3,4-methylene-dioxybenzyl
  (f) 2-furoyl
  (g) 3,4,5, -trimethoxybenzoyl
  (h) alkoxycarbonyl having up to 5 carbon atoms
  (i) (2-methyl-2-propenyl)-oxycarbonyl, or
  (j) hydroxyalkyl oxycarbonyl having 2 to 5 carbon atoms;

$R^2$ is hydrogen, dialkylamino having identical alkyl groups each having 1 to 4 carbon atoms, piperazino substituted in the 4-position by
  (a) alkyl having 1 to 3 carbon atoms
  (b) β-hydroxyethyl
  (c) 2-(1,3-dioxolan-2-yl)-ethyl
  (d) phenyl, or
  (e) 3,4-methylene-dioxy-benzyl, or $R^2$ is pyrrolidino, piperidino, 4hydroxy-piperidino, morpholino piperazino, [N-(1-ethinyl-cyclohexyl)]-amino, [N-(4-methylpiperazino)]-amino, [N-(dialkylaminocyclohexyl]-amino wherein each alkyl has 1 to 3 carbon atoms,

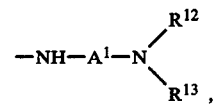

wherein $A^1$ is alkylene having 2 or 3 carbon atoms or such alkylene mono-substituted by hydroxy and $R^{12}$ and $R^{13}$, taken alone, are each alkyl having 1 to 3 carbon atoms, or, taken together with the nitrogen atom to which they are attached, are morpholino,
or $R^2$ is

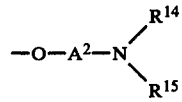

where $A^2$ is straight-chain alkylene having 2 or 3 carbon atoms and $R^{14}$ and $R^{15}$ taken alone, are respectively hydrogen and cyclohexyl, or, taken together with the nitrogen atom to which they are attached, are morpholino;
$R^3$ is hydrogen or methoxy; and
$R^4$ is methyl, phenyl, or methoxyphenyl.

2. A compound or salt as in claim 1 wherein $R^1$ is piperazino or piperazino substituted in the 4-position by alkyl having 1 to 3 carbon atoms and
$R^2$ is piperidino, morpholino, piperazino, piperazino substituted in the 4-position by alkyl having 1 to 3 carbon atoms, or

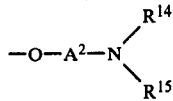

3. The compound defined in claim 1 which is 1-phenyl-2-(1-piperazinyl)-indole 3-carboxylic acid (4-methyl)-piperazide.

4. The compound defined in claim 1 which is 1-phenyl-2-(1-piperazinyl)-indole 3-carboxylic acid piperazide.

5. The compound defined in claim 1 which is 2-[4-(2-(1,3-dioxolan-2-yl)-ethyl)-1-piperazinyl]-1-phenyl-indole 3-carboxylic acid (4-methyl)-piperazide.

6. The compound defined in claim 1 which is 1-phenyl-2-(1-piperazinyl)-indole 3-carboxylic acid-[4-(3,4-methylene-dioxybenzyl)]-piperazide.

7. A pharmaceutical composition for treating arrhythmia or hypertension, which composition comprises an effective amount of a compound or salt as in claim 1 and a pharmaceutical carrier.

8. A method for treating arrhythmia or hypertension in a patent suffering therefrom, which method comprises administering to said patient an effective amount of a compound or salt as in claim 1.

* * * * *